United States Patent
Price

[19]

[11] Patent Number: 6,141,575
[45] Date of Patent: Oct. 31, 2000

[54] ELECTRODE ASSEMBLIES

[76] Inventor: Michael A. Price, 9988 Voyager Way, Cincinnati, Ohio 45252

[21] Appl. No.: 09/113,417

[22] Filed: Jul. 10, 1998

Related U.S. Application Data

[62] Division of application No. 08/911,818, Aug. 15, 1997, Pat. No. 5,995,861
[60] Provisional application No. 60/024,060, Aug. 16, 1996, abandoned.

[51] Int. Cl.⁷ .................................................. A61B 5/0908
[52] U.S. Cl. .................... 600/372; 600/391; 600/382; 600/392; 600/393; 600/394
[58] Field of Search ..................................... 607/149–153; 600/372, 382–397

[56] References Cited

U.S. PATENT DOCUMENTS

| | | |
|---|---|---|
| 4,121,575 | 10/1978 | Mills et al. . |
| 4,498,480 | 2/1985 | Mortensen . |
| 4,593,698 | 6/1986 | Athans . |
| 4,854,323 | 8/1989 | Rubin . |
| 5,224,479 | 7/1993 | Sekine . |
| 5,341,806 | 8/1994 | Gadsby et al. . |
| 5,445,149 | 8/1995 | Rotolo et al. . |
| 5,465,727 | 11/1995 | Reinhold, Jr. . |
| 5,507,290 | 4/1996 | Kelly et al. . |
| 5,511,548 | 4/1996 | Riazzi et al. .............................. 607/152 |
| 5,921,925 | 7/1999 | Cartmell et al. ......................... 600/391 |
| 5,928,142 | 7/1999 | Cartmell et al. ......................... 600/372 |

*Primary Examiner*—Linda C. M. Dvorak
*Assistant Examiner*—David M. Ruddy
*Attorney, Agent, or Firm*—Michael A. Price

[57] ABSTRACT

Electrode assemblies are particularly used with a precordial overlay to obtain a quick and accurate positioning of electrodes for an electrocardiographic test. Each electrode assembly comprises an electrode to receive a lead wire, an underlying non-conductive pad secured to the electrode, and an overlying plastic sheet secured to the electrode in a manner whereby its peripheral areas are unattached. Preferably, the electrode assembly also has an underlying adhesive layer secured to the non-conductive pad and a removable backing strip. The precordial overlay has a set of slots in which the electrode assemblies are slidably mounted. The underlying non-conductive pad and the overlying plastic sheet of the assemblies effectively trap the electrode assemblies in the slots to allow sliding electrode movement. The sliding movement of the electrodes allows for limited but quick movement from an approximate chest area location to a precise chest area location for a reliable electrocardiographic test.

20 Claims, 3 Drawing Sheets

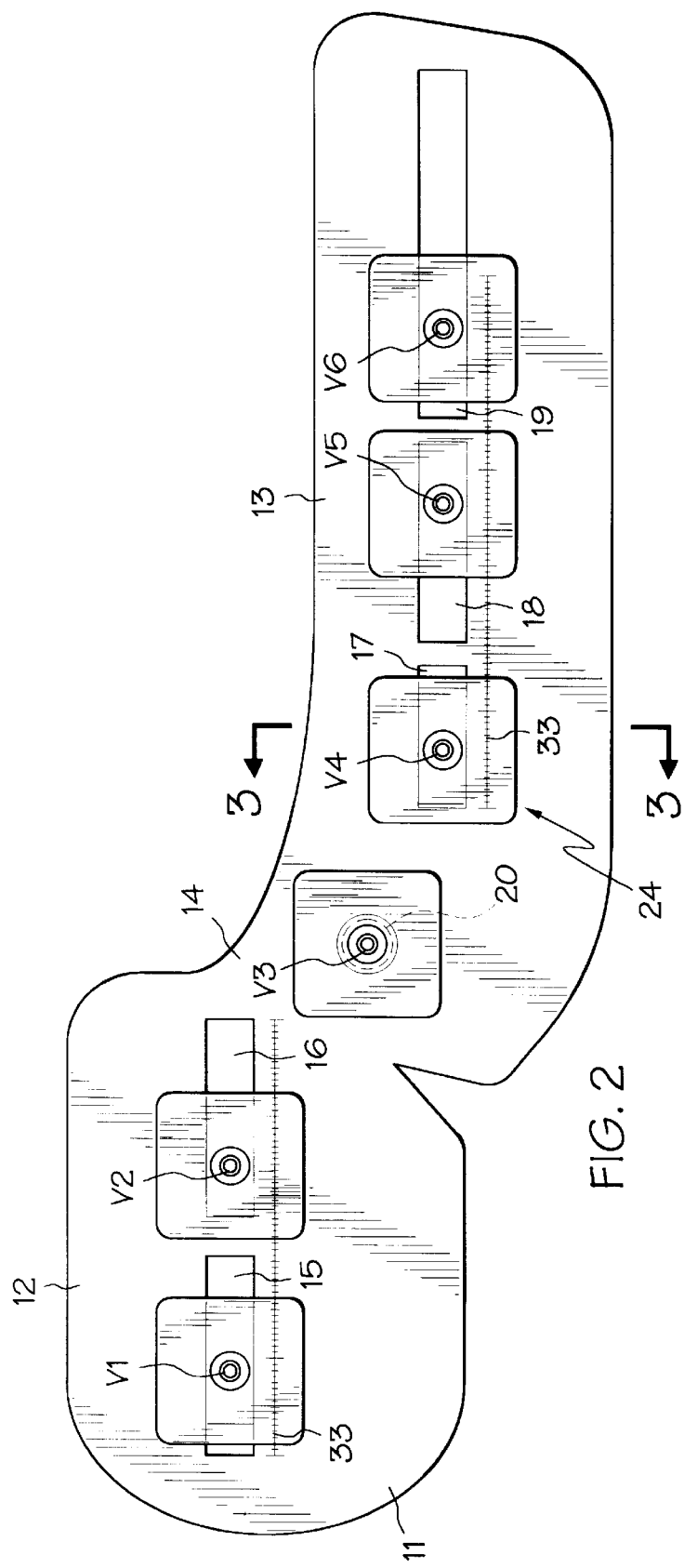
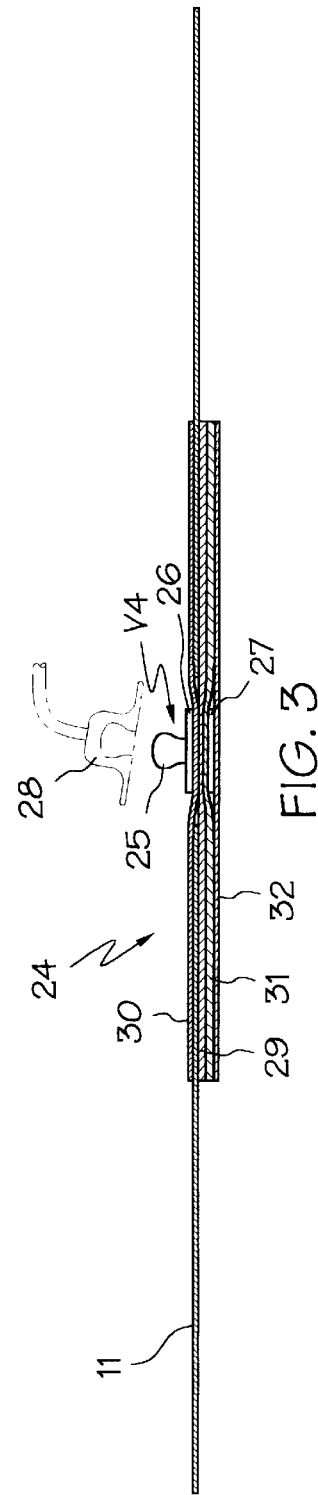
FIG. 2
FIG. 3

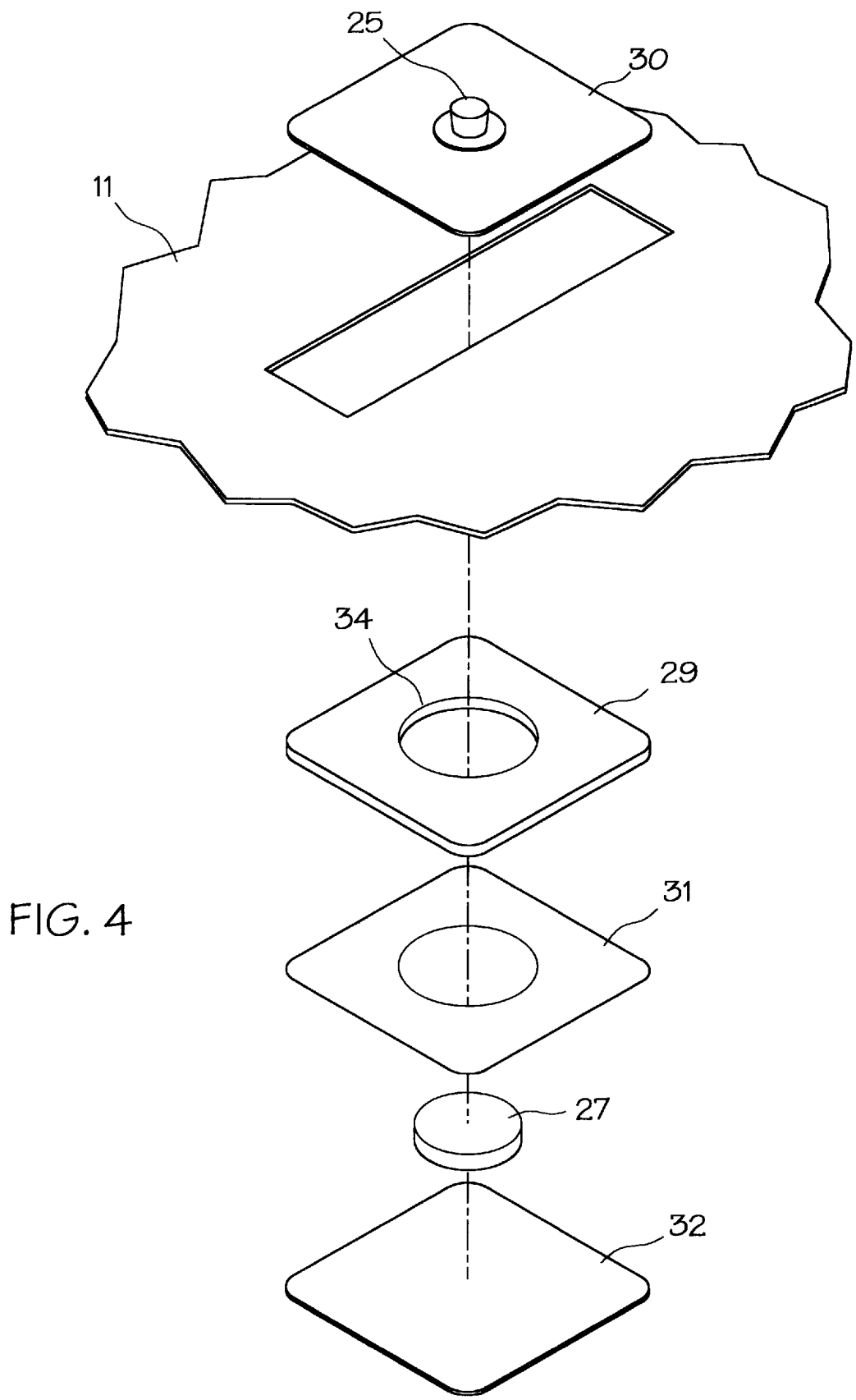

ELECTRODE ASSEMBLIES

This is a division of "Precordial Overlay For Positioning Electrocardiograph Electrodes", Ser. No. 08/911,818, filed Aug. 15, 1997 now U.S. Pat. No. 5,995,861 which claims the benefit of U.S. Provisional Application No. 60/024,060, filed Aug. 16, 1996, now abandoned.

FIELD OF THE INVENTION

This invention relates to electrode assemblies used with electrocardiographs to perform an electrocardiographic analysis on a patient. For particularly, the invention relates to electrode assemblies used with a precordial overlay to quickly and properly position on the patient electrodes which lead to the electrocardiograph.

BACKGROUND OF THE INVENTION

An electrocardiograph is a diagnostic instrument widely used in the medical field. Electric pulses generated by an individual's heart are transformed by the electrocardiograph to a recording on paper or a monitor screen to obtain an electrocardiogram, commonly referred to as an ECG. A trained medical personnel is able to interpret the ECG and detect any abnormality in the individual's heart.

Obtaining an ECG from a patient is a standard procedure used in most routine physical examinations. Emergency medical personnel, e.g. paramedics also are often called upon to obtain an ECG from an individual who has experienced chest pains. It is necessary for the medical personnel to quickly perform the test and follow standard emergency procedures depending on the test results. In some instances, the results in the form of the ECG are transmitted by cellular telemetry to a trained physician. The physician uses the test results to instruct the medical personnel on emergency procedures to be undertaken immediately or possibly to alert hospital personnel to prepare for an incoming patient. Prehospital thrombolytic screening by emergency medical personnel is well recognized in the medical field as an invaluable aid to saving lives.

It is imperative that electrodes which are placed on the patient as a part of obtaining an ECG be properly positioned. Mispositioned electrodes can alter ECG tracings and lead to possible errors in a diagnosis. Current procedures in most locales require that twelve electrodes be properly positioned at various locations on the patient. Positioning of the twelve electrodes by the technician in the physician's office is time consuming, but with patience can be correctly done. The emergency medical personnel who is working under more stressful conditions, however, has a much more difficult time in quickly and precisely positioning the individual electrodes.

There have been attempts by others to develop an article which acts as an aid in quickly and precisely positioning electrodes on a patient as part of an electrocardiographic test. U.S. Pat. Nos. 4,854,323 and 5,341,806 disclose electrode strips which are flexed to follow the patient's chest contour and seemingly to position each electrode in the proper anatomical location. U.S. Pat. Nos. 5,224,479 and 5,445,149 disclose harness-type devices which strap onto the patient's chest. Associated electrodes are said to be properly positioned. U.S. Pat. Nos. 4,121,575, 4,498,480 and 4,593,698 disclose articles which are intended to properly position six electrodes on the patient's chest. Means are provided to fine adjust the precise locations of the six electrodes. It is apparent, though, that quick and reliable electrode positionings are not easily accomplished with the known articles, especially by emergency medical personnel who must work under stressful conditions.

In accord with a demonstrated need, there has been developed electrode assemblies for use primarily by emergency medical personnel to aid them in quickly and precisely positioning electrodes on a patient as part of obtaining an ECG. The electrode assemblies are economical to produce, are easy to use and are effective for their intended function.

SUMMARY OF THE INVENTION

Electrode assemblies of the invention comprise an electrode, an underlying non-conductive pad secured to the electrode and further having an approximately centered cut-out to provide a communication means between the electrode and the patient, and an overlying semi-rigid plastic sheet securely fixed to the electrode with peripheral areas of the plastic sheet unattached for limited movement. In one embodiment, an adhesive layer further underlies the non-conductive pad. A precordial overlay used by medical personnel facilitates the quick and precise positioning of the electrode assemblies on a patient. The overlay is an elongated band configured to lie flat on the patient's chest. A set of the electrode assemblies of the invention is adjustably mounted on the band. The elongated band has a first generally rectangular-shaped section, a second generally rectangular-shaped section, and an intermediate section connecting together the first and second sections. The sections slidably hold the electrode assemblies. All the electrode assemblies are capable of limited adjusting movement in their respective sections of the elongated band prior to use.

The overlay's configuration is conducive to a medical personnel placing it on a patient's chest so that its associated electrode assemblies are all in the approximate correct locations for an electrocardiographic test. A series of quick manual manipulations of the electrode assemblies positions each one in the precise location for the test.

BRIEF DESCRIPTION OF THE DRAWINGS

FIG. 2 is a top plan view of the electrode assemblies and the precordial overlay of FIG. 1.

FIG. 3 is a view in section of an electrode assembly taken along line 3—3 of FIG. 2.

FIG. 4 is an exploded view of the electrode assembly of FIG. 3.

DETAILED DESCRIPTION OF THE INVENTION

Figure 1:
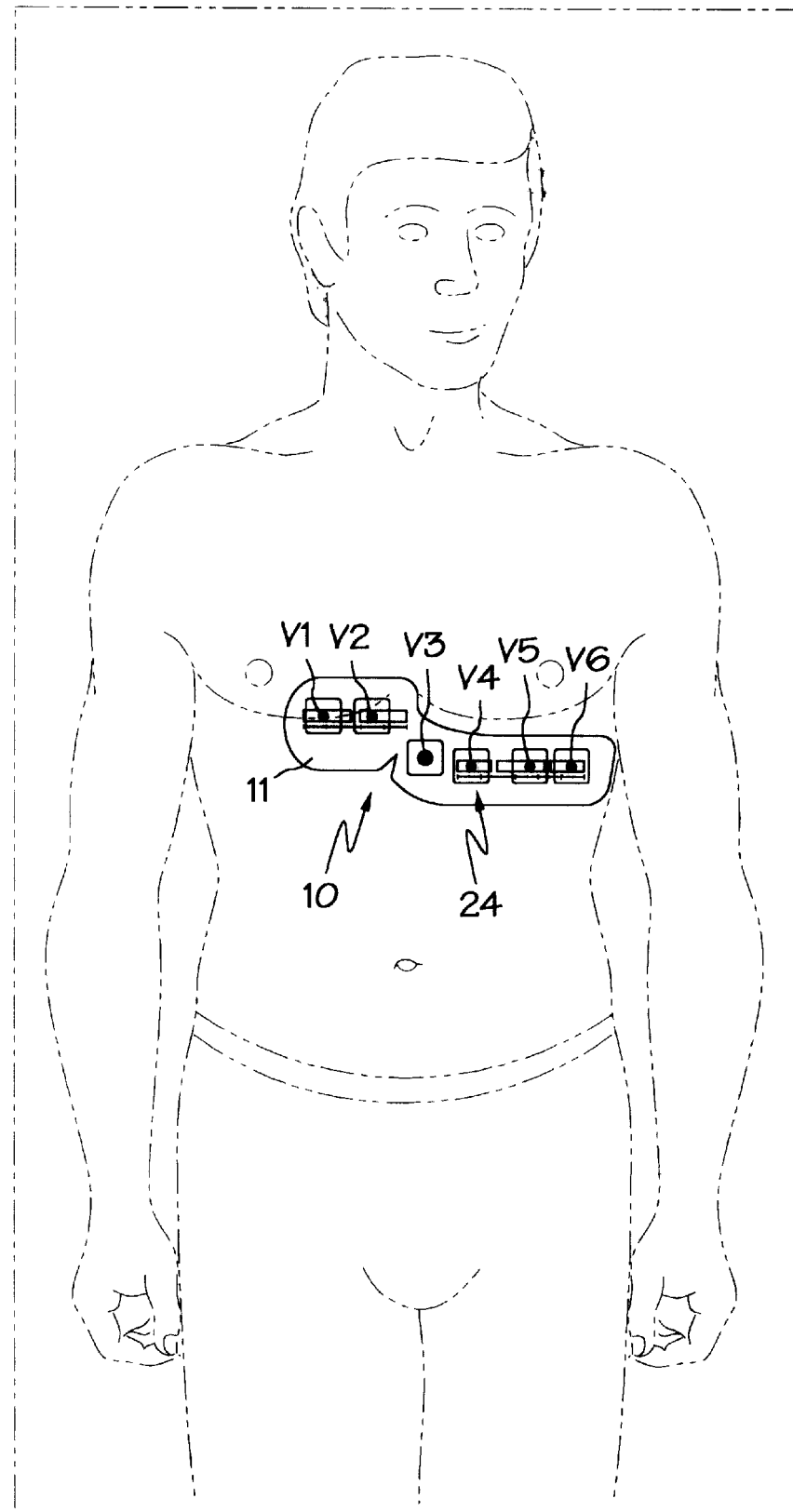
FIG. 1 is an environmental view of six electrode assemblies of the invention positioned on a precordial overlay which is lying on a prone patient's chest and in position for an electrocardiographic test.

The electrode assemblies of the invention are used with a precordial overlay for quick and proper placement of electrodes on a patient who is having an electrocardiographic test performed. The electrode assemblies and the precordial overlay are primarily used by emergency medical personnel who often must quickly obtain an ECG. They can as well be used by medical personnel in a doctor's office setting as part of a routine physical examination.

The precordial overlay is depicted in the figures. It comprises an elongated band shaped to overlie a patient's chest and a plurality of electrode assemblies. The electrode assemblies are adjustably mounted on the elongated band. In a highly preferred embodiment depicted in FIG. 1, five electrode assemblies are slidably positioned in linear cut-outs while one electrode assembly is slidably positioned in a circular cut-out. The precordial overlay's configuration allows emergency medical personnel to place the elongated band onto the patient's chest in the correct gross approximate location and then readily fine adjust the individual electrode assemblies with their electrodes in precise chest locations.

Other electrodes used in conventional twelve lead electrocardiographic tests are not shown in FIG. 1. As well known, they are individually positioned at more remote body locations as currently done and are not a part of the invention.

With reference to FIG. 1, the precordial overlay 10 comprises an elongated band 11 and six electrodes identified by their medical nomenclature as V1–V6. The electrode assemblies of the invention as described in detail below include the electrodes V1–V6. The band 11 is thin and substantially flat. It is also sufficiently flexible to follow the contour of a patient's chest. As best seen in FIG. 2, it has a first generally rectangular-shaped section 12, a second generally rectangular-shaped section 13 and an intermediate section 14. The two generally rectangular-shaped sections are off-set from one another and extend in the same longitudinal direction. The intermediate section 14 connects the first and second generally rectangular-shaped sections 12 and 13. The shape of the band generally coincides with the area of the chest where the electrodes V1–V6 must be positioned to obtain a reliable ECG.

The exact size of the elongated band is dependent on the size of the patient being tested, taking into consideration sex, age and body weight. Generally, because of the electrodes adjustability as described below, two sizes of the precordial overlay are adequate. A larger size is used for adults and a smaller size is used for children under the age of 14. Routine experimentation only is needed to determine the exact dimensions of the elongated band to meet its stated objectives.

The elongated band forming a part of the precordial overlay is made of a non-conductive material. A synthetic polymeric film is preferred because of its low material cost and capability of being given a desired shape by mass production techniques such as die-cutting. The precordial overlay of the invention is disposable primarily because the elongated band is capable of being produced at a reasonable cost. Polyethylene, polypropylene, polyvinylchloride, polyacrylate, polytetrafluoroethylene, nylon and polyester are examples of suitable polymeric films. A polyester film available as Mylar is particularly preferred.

Discreet cut-outs are provided in the body of the elongated band to accommodate the electrodes. Linear cut-outs 15 and 16 in the first generally rectangular-shaped section 12 are configured to receive electrodes V1 and V2 and allow them to laterally slide for precise positioning purposes. The cut-outs 15 and 16 are approximately centered in the first section 12 and run in the same lateral direction. One cut-out can be used in place of the two cut-outs, though is less preferred. Each cut-out 15 and 16 has a length to allow at least about 1.0 inch of electrode lateral movement. Preferably, the cut-outs 15 and 16 are each about 1.5 inches to about 2.5 inches long and about 0.5 inches to about 1.0 inches wide.

Linear cut-outs 17, 18 and 19 in the second generally rectangular-shaped section 13 are configured to receive electrodes V4, V5 and V6 in a manner which allows them to slide within their respective cut-out until properly positioned for the particular patient. Cut-outs 17, 18, and 19 each have a length to allow at least about 1.0 inch of electrode lateral movement. Preferably. cut-out 17 is about 1.5 inches to about 2.0 inches long. Preferably, cut-out 18 is about 1.5 inches to about 2.5 inches long. Preferably, cut-out 19 is about 1.5 inches to about 5.5 inches long. All three cut-outs are about 0.5 inches to about 1.0 inches wide. Each cut-out allows only limited lateral movement of its associated electrode. One cut-out extending the length of cut-outs 17–19 can be used instead of the three cut-outs 17–19. However, the three separate cut-outs are preferred to provide added precision in positioning of each of the electrodes V4, V5 and V6.

The cut-out 20 (shown in dotted line form) in the intermediate section 14 is dimensioned to receive an electrode and slidably hold it in position. The cut-out 20 is generally circular in shape with an about 0.5 inches to about 1.5 inches diameter. This relatively small cut-out is sufficient to allow limited movement of the electrode V3 in two directions.

When properly positioned on the patient's chest, the cut-outs 15 and 16 in the first section 12 overlie the patient's fourth rib and the cut-outs 17–19 in the second section 13 overlie the patient's fifth rib. The cut-out 20 in the intermediate section 14 overlies an intercostal area between the fourth and fifth ribs or slightly overlies the fifth rib. It should be apparent that trained medical personnel can very quickly place the precordial overlay on a patient's chest so that the six cut-outs overlie the correct chest area. It is then just a matter of laterally moving electrodes V1, V2, V4, V5 and V6 to a precise location known by the medical personnel. The electrode V3 must be moved laterally and longitudinally, though the precise positioning is readily accomplished.

The electrodes V1–V6 are commercially available. As best seen in FIGS. 3 and 4, they have a conductive metal post 25 and a lower conductive plate 26. An optional, underlying foam disk 27 substantially saturated with a conducting gel covers the underside of the plate 26. In accord with this invention, each of the electrodes V1–V6 is a part of an electrode assembly 24. Each electrode assembly 24 is designed to move within one of the cut-outs of the precordial overlay described above. The assemblies also include an underlying non-conductive pad 29 and an overlying clear plastic sheet 30. Preferably, an underlying adhesive layer 31 and a backing strip 32 are found on the electrode assembly 24 to hold the assembly to the patient during use. Each of the components of the electrode assembly 24 is described in detail below.

The vertically extending conductive metal post 25 receives a cap head 28 of a lead or wire which is connected to the electrocardiograph. The post has a diameter less than the width of a cut-out in the precordial overlay. This facilitates grasping the electrode and manually moving the electrode assembly in the cut-out. The lower conductive plate 26 can take on different forms. It can, for example, be a flat metal disc as shown. The post 25 and plate 26 can be an integral unit or separate components joined together. The underlying foam disk 27 is secured to an underside of the conductive plate. It is used for comfort reasons in that it is the part of the electrode that contacts the patient's skin during the electrocardiographic test. The disk 27 is substantially saturated with a conducting gel.

Still with reference to FIG. 3, the electrode V4 illustrated is mounted on a non-conductive pad 29 for ease of handling purposes. As evident in the figures, the pad has a width greater than that of the cut-out with which it is associated. The pad 29 has an approximately centered circular cut-out 34. The cut-out provides a communication means between the conductive plate 26 and the patient. In the embodiment shown wherein the foam disk 27 with the conductive gel covers the underside of the plate 26, the circular cut-out 34 is needed to receive the foam disk 27. The pad 29 itself is preferably a foam material.

A clear plastic sheet layer 30 overlies the non-conductive pad 29 and surrounds the metal post 25 of the electrode. Its width also is greater than that of the precordial overlay cut-out with which it is associated. The plastic sheet 30 is secured to the pad 29 at the conductive plate 26 only, such that its peripheral areas are free or unattached. The plastic sheet's function is to provide a means to slidably hold the pad 29 and its associated electrode V4 in the cut-out 17. A semi-rigid plastic sheet is optimum for this purpose. The electrode V4 extends up through the cut-out 17. Its associated pad 29 on the underside of the cut-out 17 and the associated plastic sheet 30 on the topside of the cut-out 17 in effect trap the electrode within the cut-out 17 of the precordial overlay 11 while allowing a sliding movement.

An adhesive means is provided to temporarily hold the precordial overlay to the patient's chest during use. A series of self-stick adhesive strips can be used on the precordial overlay's topside to extend off its peripheral edges and onto the patient's chest. This allows the overlay to be taped to the patient once the overlay is in its proper approximate location. Alternatively, a self-stick adhesive can be provided on the underside of the precordial overlay. The adhesive can cover or appear as strategically placed patches on the underside of the elongated band 11. More preferably and as illustrated, the adhesive is a part of the electrode assembly 24. The adhesive is found on the underside of at least some of the individual non-conductive pads. With reference again to FIGS. 3 and 4, an adhesive layer 31 extends up to and surrounds the underlying foam disk 27 of the electrode V4. As well known, a removable full piece or two part split backing strip 32 is used to protect the adhesive layer during shipping and storage. When the precordial overlay is ready for placement on the patient, the backing 32 is removed to expose the adhesive layer 31.

Preferably, and with reference to FIGS. 1 and 2, numeric scales 33 are printed onto the elongated band 11 of the precordial overlay. The scales are located just below the cut-outs 15 and 16 in the first generally rectangular-shaped section 12 and below the cut-outs 17–19 in the second generally rectangular-shaped section 13. The numeric scales are used to record precise electrode placements in case a second reading is needed to verify an initial ECG.

In use, the medical emergency personnel initially and temporarily positions the elongated band of the precordial overlay 10 on a patient using well known anatomical landmarks, e.g. a sternum notch. The V1 and V2 electrodes are first adjusted for the particular patient. Next, the V4–V6 electrodes are adjusted. The adjustments are made by placing the elongated band onto or at least near the patient's chest. Once the six electrodes are positioned and adjustments made, the backing is removed from the adhesive layer on the underside of each of the pads to expose the adhesive layers. The elongated band is then placed on the patient where it remains until the ECG is obtained. After use, the precordial overlay and electrode assemblies are discarded.

From the above description, it should be apparent the precordial overlay and the electrode assemblies serve a very real need, especially in the emergency medical field. Paramedics and other medical personnel can be trained in proper use of the overlay in a relatively short time. Proper placement of electrode assemblies with their electrodes V1–V6 on a patient by a properly trained medical personnel is assured. Furthermore, repeatable ECG test results are a near certainty. The precordial overlay and electrode assemblies are inexpensive to produce and, resultingly, can be discarded after only one use. This disposable nature of the overlay and assemblies eliminates any concern for sanitation in that it is not necessary to clean the product after use.

Having described the invention in its preferred embodiment, it should be clear that modifications can be made without departing from the spirit of the invention. For example, other electrode styles than that illustrated are known, including clamp electrodes and suction cup electrodes. Still other styles of electrodes are known and usable in the invention with only minor if any modification to the balance of the assembly and elongated band to accommodate them. It is not intended that the words used to describe the invention nor the drawings illustrating the same be limiting on the invention. It is intended that the invention only be limited by the scope of the appended claims.

I claim:

1. An electrode assembly for use in an electrocardiographic test wherein electrodes must be quickly and accurately positioned on a patient, said assembly comprising:
    (a) an electrode;
    (b) an underlying non-conductive pad permanently secured to the electrode; and
    (c) an overlying plastic sheet having an approximately centered area and having circumjacent peripheral areas, further said overlying plastic sheet being permanently secured in its approximately centered area to the electrode and the circumjacent peripheral areas of said plastic sheet are unattached for sliding movement.

2. The electrode assembly of claim 1 wherein the overlying plastic sheet is semi-rigid.

3. The electrode assembly of claim 2 wherein the non-conductive pad further has an approximately centered cut-out to provide a communication means between the electrode and the patient.

4. The electrode assembly of claim 3 wherein the electrode has a conductive metal post and a conductive plate.

5. The electrode assembly of claim 4 wherein the non-conductive pad is made of a foam material.

6. The electrode assembly of claim 4 further having a conductive foam disk secured to an underside of the conductive plate.

7. The electrode assembly of claim 6 wherein the foam disk is substantially saturated with a conducting gel.

8. The electrode assembly of claim 1 further comprising an adhesive layer on the underside of the non-conductive pad, further said adhesive layer having a removable backing strip to protect the adhesive layer during shipping or storage of the electrode assembly.

9. An electrode assembly for use in an electrocardiographic test wherein electrodes must be quickly and accurately positioned on a patient, said assembly comprising:
    (a) an electrode having a conductive metal post and conductive plate with a foam disk secured to an underside of the conductive plate, further said foam disk substantially saturated with a conducting gel;
    (b) an underlying non-conductive foam pad permanently secured to the electrode, said foam pad further having an approximately centered cut-out to receive the foam disk of the electrode;
    (c) an overlying plastic sheet fixed in an approximately centered area to the conductive metal post and conductive plate whereby peripheral areas of said plastic sheet are unattached;

(d) an adhesive layer on the underside of the non-conductive foam pad; and (e) a removable backing strip on the adhesive layer to protect said adhesive layer during shipping or storage of the electrode assembly.

10. The electrode assembly of claim 9 wherein the overlying plastic sheet is semi-rigid.

11. The electrode assembly of claim 10 wherein the overlying plastic sheet is clear.

12. The electrode assembly of claim 9 wherein the non-conductive pad is made of a foam material.

13. A one-piece electrode assembly for use with a precordial overlay wherein the overlay has a set of discreet cut-outs to receive electrodes and to allow the electrodes to be slidably positioned on a patient, said assembly comprising:

(a) an electrode;

(b) an underlying non-conductive pad secured to the electrode; and (c) an overlying plastic sheet having an approximately centered area and having peripheral areas circumjacent the approximately centered area and further said overlying plastic sheet is secured in its approximately centered area to the electrode and the peripheral areas of said plastic sheet are unattached to the underlying non-conductive pad, whereby the underlying non-conductive pad and the overlying plastic sheet allow the electrode assembly to be positioned in one of the discreet cut-outs of the precordial overlay in a manner wherein the electrode is trapped in the discreet cut-out with limited electrode sliding movement within said discreet cut-out.

14. The one-piece electrode assembly of claim 13 wherein the overlying plastic sheet is semi-rigid.

15. The one-piece electrode assembly of claim 14 wherein the electrode has a conductive metal post and a conductive plate.

16. The one-piece electrode assembly of claim 14 wherein the non-conductive pad has an approximately centered cut-out to provide a communication means between the electrode and the patient.

17. The one-piece electrode assembly of claim 16 wherein the non-conductive pad is made of a foam material.

18. The one-piece electrode assembly of claim 15 further having a conductive foam disk secured to an underside of the conductive plate wherein said foam pad is substantially saturated with a conducting gel.

19. The one-piece electrode assembly of claim 13 further comprising an adhesive layer on the underside of the non-conductive pad.

20. The electrode assembly of claim 1 wherein the overlying plastic sheet is unattached in its peripheral areas to the underlying non-conductive pad.

* * * * *